United States Patent [19]
Simons et al.

[11] Patent Number: 5,334,182
[45] Date of Patent: Aug. 2, 1994

[54] PULMONARY ARTERY CATHETER MONITORING BRIDGE

[75] Inventors: R. Kaye Simons, Saginaw; Frazer A. Wadenstorer, Millington, both of Mich.

[73] Assignee: Perry Creek Group Corporation, Bridgeport, Mich.

[21] Appl. No.: 939,143

[22] Filed: Sep. 2, 1992

[51] Int. Cl.$^5$ .................. A61M 1/00; A61M 5/00; A61M 25/00; F16K 5/00
[52] U.S. Cl. .................. 604/32; 604/248; 604/283; 137/625.47
[58] Field of Search .............. 604/30, 32-34 80, 604/173, 189, 246, 248, 264, 280, 283, 258, 256, 257; 137/625.47

[56] References Cited

U.S. PATENT DOCUMENTS

| | | | |
|---|---|---|---|
| 3,699,964 | 10/1972 | Ericson | 604/323 X |
| 3,834,372 | 7/1974 | Turney | 604/248 X |
| 4,150,672 | 4/1979 | Whitney et al. | 604/246 X |
| 4,298,001 | 11/1981 | Hargest, III et al. | |
| 4,489,721 | 12/1984 | Ozaki et al. | |
| 4,638,539 | 1/1987 | Palmer | |
| 4,734,091 | 3/1988 | Boyle et al. | 604/54 |
| 4,823,833 | 4/1989 | Hogan et al. | |
| 4,892,524 | 1/1990 | Smith | 604/246 |
| 4,994,035 | 2/1991 | Mokros | 604/118 |
| 5,070,871 | 12/1991 | Manicom | |
| 5,104,387 | 4/1992 | Pokorney et al. | 604/248 |
| 5,140,982 | 8/1992 | Bauman | 128/205.13 |

Primary Examiner—John D. Yasko
Assistant Examiner—Adam J. Cermak
Attorney, Agent, or Firm—Harness, Dickey & Pierce

[57] ABSTRACT

A catheter monitor bridge is provided which allows for rapid identification of intravenous lines. The bridge has color-keyed fluid routing paths indicated on the bridge so that a caretaker can easily connect intravenous lines to the bridge and can readily manipulate the flow of fluids between the intravenous lines.

9 Claims, 1 Drawing Sheet

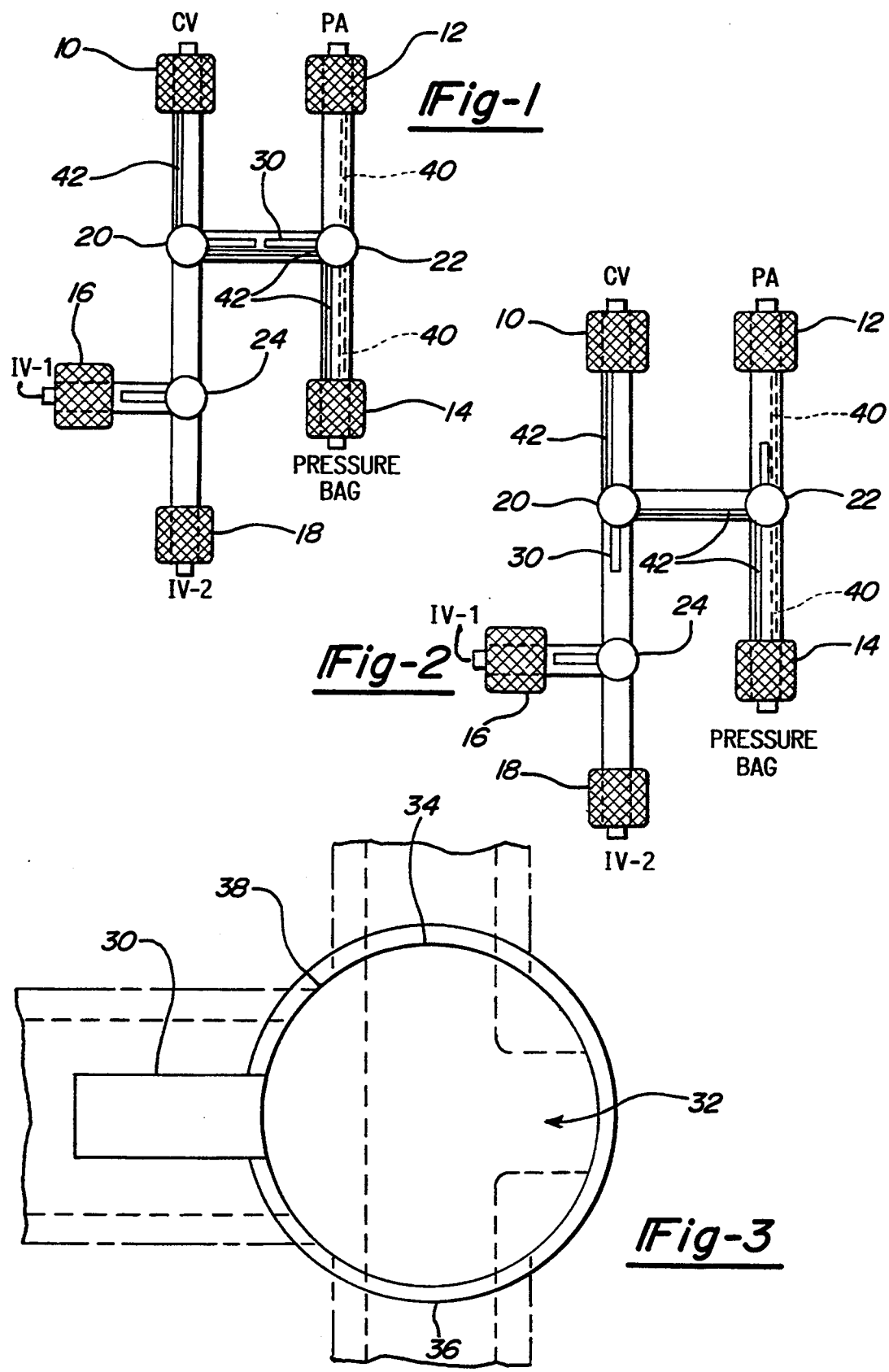

PULMONARY ARTERY CATHETER MONITORING BRIDGE

FIELD OF THE INVENTION

The present invention relates to a catheter bridge, and more particularly to a pulmonary artery catheter monitoring bridge adapted to provide for rapid identification of intravenous lines so that care personnel can infuse medication and perform diagnostic readings more readily.

BACKGROUND OF THE INVENTION

In the field of intensive critical care, the ability of care personnel to respond to crises can be hampered if the caretaker is required to trace intravenous tubes. For example, it is quite common for a cardiac critical care patient to have a multiple lumen catheter inserted through a central vein into the heart and on into the pulmonary artery, where each lumen of the catheter is guided into different areas of the heart for the purposes of hemodynamic monitoring. One commonly used catheter employs four lumens, two of those lumens adapted to allow blood and fluids to flow in and out of the patient, and the other two lumens adapted to operate internal diagnostic devices such as a thermistor and occluding balloon for determining pulmonary wedge pressure. Of the two lines which transmit fluids, one lumen is adapted to provide a means for measuring pulmonary artery distal pressure and the other lumen is adapted to measure central venous pressure.

These multiple lumen catheters are commonly attached to a stop cock valve assembly, where the caretaker manipulates the positions of the stop cock valves in order to direct the flow of fluids. For example, configuring these valves so that a fluid path is provided between the lumen inserted in the central vein and the pressure bag allows for the caretaker to measure central venous pressure. Similarly, arranging the valves so that a path is provided between the pulmonary artery and the pressure bag allows for distal pressure to be measured. Finally, the valves can be arranged so that a fluid path is provided between injecting ports and the various blood fluid lines for the purposes of infusing medication.

Because caretakers are often required to obtain pressure readings and infuse medications during a crisis situation, it is important that the caretaker be able to rapidly identify the location of the various intravenous lines and establish the proper fluid communication paths through the stop cock valve assembly. Unfortunately, most caretakers are required to manually construct these monitoring bridges by assembling a number of individual stop cock valves into a bridge assembly. This poses two problems. The first problem is that each caretaker may choose to use a different configuration of valves to achieve the same fluid routing bridge. As a result, caretakers are often confronted with configurations assembled by a different caretaker and which are unfamiliar to them. This leads to the second problem, which is an increase in the time it takes the caretaker to respond to a crisis situation, since the caretaker must first decipher the configuration of the stop cock valve bridge assembly before being able to determine the proper combination of valve positions necessary to achieve the desired fluid flow path. Thus, confronting a caretaker with an ad hoc configuration of stop cock valves increases the risk that erroneous pressure readings may be taken or that injections may be infused into the wrong lines. It would therefore be advantageous to provide for a catheter monitor bridge where the configuration of the lumens and the valves would be easy to identify, and the manner in which the stop cock valves need to be manipulated in order to route the fluids for the various pressure readings and infusions would be readily apparent to a caretaker. In this way, caretakers would be better able to respond to a crisis situation promptly without risking misidentification of the bridge components.

SUMMARY OF THE INVENTION

It is therefore an object of the present invention to provide for a catheter monitor bridge adapted for use in intensive critical care situations. The monitor bridge of the present invention has a number of luer lock connectors for attaching intravenous lines. Disposed between the connectors are several stop cock valves, where the valves can be manipulated to route fluid flow between various combinations of lumens. Markings are provided on the monitor bridge to indicate the proper valve positions for at least one configuration of fluid flow, thereby allowing the caretaker to identify and effectuate the proper valve positions during a crisis situation.

One advantage of the present invention is that care personnel will not have to manually assemble stop cock valves to form the catheter bridge. Another advantage of the present invention is that the configuration of the monitor bridge allows for rapid identification of the various intravenous lines, reducing the amount of time required to respond to a crisis situation. A further advantage is that ready identification reduces the risk that erroneous pressure readings may be taken or improper medications administered. Another feature of the present invention is that the valve fluid routing marks are color-keyed to match the color of commonly used intravenous tubes.

BRIEF DESCRIPTION OF THE DRAWINGS

Other features and advantages of the present invention will become apparent from the following description and appended claims, taken in conjunction with the accompanying drawings in which:

FIG. 1 is an illustration of the catheter monitor bridge with the stop cock valves positioned such that pulmonary artery pressure can be monitored and an intravenous fluid can be administered to the central vein;

FIG. 2 is an illustration of the catheter monitor bridge with the stop cock valves configured such that central venous pressure is being monitored; and FIG. 3 is a detailed illustration of the manner in which a stop cock valve is ported.

DETAILED DESCRIPTION OF THE PREFERRED EMBODIMENTS

As depicted in FIG. 1, the catheter monitor bridge of the presently preferred embodiment is adapted for use with a multiple lumen pulmonary artery catheter. Commercially available from a variety of sources, the multiple lumen cardiac catheters include four lumens: one lumen for communicating blood flow from the central vein, another lumen for communicating blood flow from the pulmonary artery, a third lumen fitted with a thermistor and the fourth lumen fitted with an occluding balloon. In practice, the central vein and pulmonary artery intravenous tubes are connected to a monitoring bridge for the purpose of obtaining pressure readings and injecting solutions into the patient.

As disclosed here, the monitor bridge of the presently preferred embodiment is preferably comprised of an inert transparent, semi-transparent or translucent plastic compound. It should be inert because a variety of bodily fluids and medications may be transported through the bridge, and adverse chemicals reactions may pose a risk to the patient. It should be transparent, semi-transparent or translucent to provide a visual verification to the caretaker that fluids are flowing through the bridge in the desired manner. Being comprised of plastic, the bridge is also preferably designed to be disposable after use, since it has become customary practice in the hospital industry to dispose of such products rather than attempting to re-sterilize them after use in conjunction with a patient.

As can be seen by referring to FIGS. 1 and 2, the monitor bridge of the presently preferred embodiment, which is adapted for use in conjunction with a four lumen hemodynamic monitoring catheter, has five connectors 10-18. It can be appreciated by one of ordinary skill in the art that the connections should be adapted to firmly receive the intravenous tubes, so as to prevent inadvertent disconnection of the monitor bridge from the intravenous tubes. The first connector 10 is connected to the intravenous line coming from the central vein, the second connector 12 is connected to the intravenous line from the pulmonary artery and the third connector 14 attaches to a pressure bag. The fourth and fifth connectors 16, 18 are provided to allow for the administration of two different intravenous fluids, denoted herein as IV-1 and IV-2.

In order to route the flow of fluids between the various connectors 10-18, stop cock valves are provided. The first valve 20 controls the routing of fluids into the central vein, while the second valve 22 controls the routing of fluids to the pulmonary artery. The third valve 24 allows the caretaker to select which intravenous fluid is to be administered to the patient.

The bridge is preferably presented as an integral unit, with the connectors 10-18 and valves 20-24 arranged as depicted. This alleviates the need of the caretaker to perform any assembly beyond the connection of the intravenous lines. Also, the risk that the bridge may become disassembled or that bacteria may infiltrate the intravenous system through connection points in the bridge is avoided when presented as an integral unit. These advantages will be set forth in greater detail later in this specification. However, to the extent that in may be desirable to present the bridge as a partially or wholly disassembled unit which is assembled either by the caretaker or some intermediary prior to the caretaker, the foregoing description of the appearance and functionality of the monitor bridge should be viewed as being illustrative of one, albeit preferred, manner of embodying this invention.

Referring now to FIGS. 1 and 3 in unison, it can be seen that the handle 30 of the stop cock valve indicates the path for which flow of fluid is occluded. More particularly, the valve has internal porting 32 such that fluid can be communicated between any two ports 34, 36 and that the flow of fluid to the third port 38 is occluded.

As depicted in FIG. 1, the stop cock valves are arranged such that a pulmonary artery pressure reading can be obtained, since the fluid flow is directed from the pulmonary artery tube connection 12 through the second valve 22 to the connector 14 to which the pressure bag is attached. Also as depicted in FIG. 1, solution from the second intravenous administration tube can flow through the connector 18, through the third valve 24, through the first valve 20 to the connector attached to the tube leading into the patient's central vein 10.

As illustrated in FIG. 2, a central venous pressure reading is obtained by arranging the stop cock valves as shown. This provides for the flow of fluids from the central vein into the connector 10, through the first and second valves 20, 22 and into the connector 14 leading to the pressure bag.

From the illustrations in FIGS. 1 and 2, several advantages of the present invention will be appreciated. First, the configuration of intravenous tube connectors and stop cock valves provided in the presently preferred embodiment represents the configuration of valves most frequently required in a critical care situation. By providing a preassembled bridge, the presently preferred embodiment alleviates the need for the caretaker to manually assemble stop cock valves in order to arrive at this configuration. This alleviates the problem of one caretaker being confronted with an unfamiliar configuration that was assembled by a different caretaker.

Another advantageous feature of the presently preferred embodiment is that the physical presentation of the bridge facilitates rapid identification of the various lines. As depicted herein, the bridge of the presently preferred embodiment generally resembles an H, with the leg of the H adapted to be connected to the pulmonary artery tube being shorter than the leg of the H to which the central vein tube attaches. In practice, when required to manually assemble their own stop cock valve bridge assembly, caretakers usually configure the valve bridge such that the intravenous administration lines are closer to the central venous line than to the pulmonary artery line. Thus, the catheter monitoring bridge of the presently preferred embodiment provides for a configuration which is easily recognizable by caretakers. In short, a caretaker can simply glance at the bridge to determine the manner in which the intravenous lines are interconnected: the top of the "long" leg attaches to the central venous line, the bottom of the "long" leg attaches to the intravenous lines, the top of the "short" leg attaches to the pulmonary artery line and the bottom of the "short" leg attaches to the pressure bag. Thus, when initially hooking up the monitor bridge to the various catheters, the caretaker can easily discern which tubes should be connected to which connectors. Furthermore, once the monitor bridge has been installed and the catheters attached to the patient, the caretaker can easily discern which lines are connected to the various monitoring and infusion sites using this same "long leg"-"short leg" visual identification method.

To further aid caretakers in the rapid identification of intravenous lines and determination of necessary stop cock valve configurations, the presently preferred embodiment provides for color-keyed identification markings. In practice, the intravenous tube associated with the pulmonary artery is commonly yellow in color. Therefore, the identification marking indicating the proper fluid path for measuring pulmonary artery pressure is indicated in yellow 40 (indicated by dash lines 40). Similarly, the intravenous tube associated with the central vein is commonly colored red. Thus, the fluid routing path which results in a central venous pressure reading is indicated with a red line 42 (indicated by solid lines 42). These color-keyed markings aid the caretaker in rapidly identifying the proper configuration of valves in order to perform the various pressure readings. For example, as depicted in FIG. 1, in order to obtain a pulmonary artery ("yellow" tube) pressure reading, the second valve 22 must have its handle 30 positioned such that it does not cover, or block out, the yellow line 40. Similarly, as depicted in FIG. 2, to obtain a central venous pressure reading, the caretaker adjusts the handles 30 of the first and second valves 20, 22 so that the handles do not lie over the red line 42. Thus, in addition to the distinctive H shape of the catheter monitor bridge of the presently preferred embodiment, the color-keyed markings further assist the caretaker in rapidly identifying the proper position of valves necessary to obtain the various pressure readings.

The color-keyed markings also assist the caretaker in initially connecting the catheter monitor bridge to the various intravenous tubes, since the connector with the yellow line 40 leading to it gets connected to the yellow pulmonary artery tube, the connector with the red line 42 gets connected to the red central venous tube and the connector having both the red and yellow lines 40, 42 gets connected to the pressure bag. It should be noted that since a wide variety of intravenous solutions may be chosen to be administered to the patient, the connectors to which the intravenous solutions attach preferably have no color markings, as is depicted herein. Of course, lines indicating the proper valve positioning for the intravenous injection ports may also be provided should the needs of a particular situation so dictate.

Because the monitor bridge is preferably comprised of a plastic compound which is at least translucent, the caretaker is provided with an additional form of confirmation that the intravenous tubes and valves are properly positioned on the bridge since the flow of fluids such as blood through the bridge can be observed through the plastic.

Still another advantage of the invention which will be appreciated by observing the presently preferred embodiment is that the integral monitor bridge itself cannot leak or become partially disassembled as would be the case with a monitor bridge manually constructed from a number of different stop cock valves. This not only reduces the chances of accidental disassembly, but also reduces the risk that bacteria may infiltrate the intravenous system through a connection site. However, to the extent that it may be preferable to provide for a bridge that is presented in a partially disassembled state, the provisions for the marking of the various flow paths aids the caretaker in properly assembling the bridge's subcomponents to form an assembled bridge.

While the presently preferred embodiment disclosed herein is adapted for use in conjunction with a multiple lumen catheter used during hemodynamic monitoring, it will be appreciated that there may be any number of additional applications in which caretaker response time and error rate can be reduced through the use of a preassembled color-keyed catheter bridge. Thus, one could exercise ordinary skill in the art to adapt the invention disclosed herein to suit the needs of a particular situation without departing from the spirit or scope of the invention disclosed herein.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

We claim:

1. An apparatus for interconnecting to and routing fluid flow between a plurality of tubings in patient hemodynamic monitoring situations, one of said tubings connected to a fluid line in communication with a central vein of a patient, another of said tubings connected to another fluid line in communication with a pulmonary artery of said patient, another of said tubings connected to another fluid line in communication with a pressure reading apparatus and the remainder of said plurality of tubings connected to at least one fluid line in communication with an intravenous solution reservoir, the apparatus comprising:

a plurality of connectors for receiving said fluid lines and said tubing;

fluid path means, disposed between said connectors, for carrying fluids to and from said connectors;

fluid routing means, disposed between said fluid path means, for routing fluid flow along said fluid path means, said path means and said routing means cooperating to selectively provide for a fluid communication path between said pulmonary artery and said pressure reading apparatus to obtain a pulmonary artery pressure reading while also selectively providing for a fluid communication path between said central vein and one of said antravenous solutions to administer said solutions to the patient, and said path means and said routing means cooperating to selectively provide for a fluid communication path between said central vein and said pressure reading apparatus to obtain a central venous pressure reading while also inhibiting fluid communication between said central vein and said at least one intravenous solutions and between said pulmonary artery and said pressure reading apparatus, wherein said fluid path means is capable of precluding exposure of said intravenous solution to the atmosphere; and route markings for identifying fluid routes along said fluid path means coincident with said selective fluid communication paths.

2. An apparatus as set forth in claim 1 wherein said fluid routing means comprises a plurality of valves, said valves for selectively occluding flow to and from one or more fluid path means and for selectively permitting fluid communication between two or more fluid path means wherein said pulmonary artery pressure reading path and said intravenous administration path may be selectively active both simultaneously and separately, and wherein when said central venous pressure reading path is active said pulmonary artery and said intravenous solution fluid lines are occluded.

3. An apparatus as set forth in claim 2 wherein each said valve includes a lever mechanically linked to the valve for indicating those fluid path means being occluded and those fluid path means wherein fluid communication is permitted.

4. An apparatus for selectively routing fluid flow between a plurality of fluid lines in patient hemodynamic monitoring situations, one of said lines connected to a central vein of a patient, another of said lines connected to a pulmonary artery of said patient, another of said lines connected to a pressure reading apparatus and the remainder of said plurality of lines connected to at least one intravenous solution reservoir, the apparatus comprising:

a plurality of fluid path means for carrying fluid between two or more fluid lines;

a plurality of connection means for connecting said fluid path means to said fluid lines;

a plurality of fluid flow routing means, each routing means disposed between two or more fluid path means, for routing fluid flow amongst said fluid path means to selectively provide for a first fluid communication path between said pulmonary artery and said pressure reading apparatus to obtain a pulmonary artery pressure reading while also selectively providing for a second fluid communication path between said central vein and one of said intravenous solutions to administer said solutions to the patient, and to selectively provide for a third fluid communication path between said central vein and said pressure reading apparatus to obtain a central venous pressure reading while also inhibiting fluid communication between said central vein and said plurality of intravenous solutions and between said pulmonary artery and said pressure reading apparatus wherein each said routing means comprises a valve, said valve being selectively manipulable to route fluid flow between two or more fluid path means wherein said first fluid communication path and said second fluid communication path may be selectively active both simultaneously and separately, and wherein said third fluid communication path is active when said first fluid communication path and said communication path is occluded, wherein said fluid path means is capable of precluding exposure of said intravenous solution to the atmosphere; and at least one fluid flow path marking for indicating to which two or more fluid path means fluid flow is routed by said routing means, said path marking corresponding to one of said fluid communication paths.

5. An apparatus as set forth in claim 4 wherein each said valve includes a lever, wherein movement of said lever changes the routing of fluid flow between two or more sets of fluid path means.

6. A method for identifying a plurality of fluid lines and for routing fluid flow between said fluid lines, one of said fluid lines communicating with a patient central vein, another of said fluid lines communicating with said patient pulmonary artery, another of said fluid lines communicating with a pressure reading apparatus and the remainder of said fluid lines communicating with at least one intravenous solution, the method comprising the steps of:

(a) connecting said fluid lines to a fluid routing bridge;

(b) identifying two or more fluid lines between which fluid communication is desired, said identified combinations including a fluid path between said pulmonary artery and said pressure reading apparatus for obtaining pulmonary artery pressure reading, a fluid path between one of said intravenous solutions and said central vein for administering said solution to said patient, and a fluid path between said central vein and said pressure reading apparatus for obtaining a central venous pressure reading; and (c) manipulating a plurality of fluid routing valves, disposed within said fluid routing bridge, to route the flow of fluid between said desired fluid lines wherein said pulmonary artery pressure reading path and said intravenous administration path may be selectively active both simultaneously and separately, and wherein when said central venous pressure reading path is active said pulmonary artery and said intravenous solution fluid lines are occluded.

7. A method as set forth in claim 6 wherein each said fluid routing valve has an indicator which indicates at least one fluid line that is occluded.

8. A method as set forth in claim 7 wherein step (b) further comprises identifying a route marking on said fluid routing bridge which indicates said fluid paths between said desired fluid lines.

9. A method as set forth in claim 8 wherein step (c) comprises manipulating the positions of said fluid routing valves such that the position of their indicators do not coincide with the position of the route marking on said fluid routing bridge, said manipulated valve positions corresponding to the route of fluid flow between said desired fluid lines through said fluid routing bridge along said indicated fluid path.

* * * * *